US012612359B2

(12) United States Patent
Guo et al.

(10) Patent No.: US 12,612,359 B2
(45) Date of Patent: Apr. 28, 2026

(54) ***CIS-PARA*-SUBSTITUTED CYCLOHEXYLAMINONITRILE SALT, PREPARATION METHOD THEREFOR AND USE THEREOF, AND METHOD FOR PREPARING PESTICIDE USING SAME**

(71) Applicants: HEBEI LANSHENG BIOTECH CO., LTD, Shijiazhuang (CN); HEBEI LANRUN PLANT PROTECTION TECHNOLOGY CO., LTD, Cangzhou (CN); HEBEI GUZHIRUN TECHNOLOGY CO., LTD, Shijiazhuang (CN)

(72) Inventors: Qingchun Guo, Shijiazhuang (CN); Zhengang Zhu, Shijiazhuang (CN); Hongyong Guo, Shijiazhuang (CN); Xin Zhang, Shijiazhuang (CN); Weiwei Liu, Shijiazhuang (CN)

(73) Assignees: LANSHENG BIOTECHNOLOGY GROUP CO., LTD., Shijiazhuang City (CN); HEBEI LANRUN PLANT PROTECTION TECHNOLOGY CO., LTD, Cangzhou (CN); HEBEI GUZHIRUN TECHNOLOGY CO., LTD., Shijiazhuang (CN)

( * ) Notice: Subject to any disclaimer, the term of this patent is extended or adjusted under 35 U.S.C. 154(b) by 415 days.

(21) Appl. No.: 18/033,114

(22) PCT Filed: Oct. 14, 2021

(86) PCT No.: PCT/CN2021/123804
§ 371 (c)(1),
(2) Date: Apr. 21, 2023

(87) PCT Pub. No.: WO2022/083494
PCT Pub. Date: Apr. 28, 2022

(65) Prior Publication Data

US 2023/0257341 A1 Aug. 17, 2023

(30) Foreign Application Priority Data

Oct. 22, 2020 (CN) ........................ 202011138765.3

(51) Int. Cl.
*C07C 255/46* (2006.01)
*C07C 253/30* (2006.01)
*C07C 253/34* (2006.01)

(52) U.S. Cl.
CPC .......... *C07C 255/46* (2013.01); *C07C 253/30* (2013.01); *C07C 253/34* (2013.01); *C07B 2200/13* (2013.01)

(58) Field of Classification Search
CPC .... C07C 255/46; C07C 253/30; C07C 253/34
See application file for complete search history.

(56) References Cited

U.S. PATENT DOCUMENTS

2012/0197035 A1 8/2012 Volz et al.

FOREIGN PATENT DOCUMENTS

| | | | | |
|---|---|---|---|---|
| CN | 103270020 | A | | 8/2013 |
| CN | 105777581 | A | | 7/2016 |
| CN | 110294692 | A | | 10/2019 |
| CN | 110691771 | A | | 1/2020 |
| EP | 3 819 289 | A1 | | 5/2021 |
| EP | 4 006 010 | A1 | | 6/2022 |
| WO | WO2019233498 | A1 | * | 12/2019 |

OTHER PUBLICATIONS

Communication pursuant to Rules 70(2) and 70a(2) EPC issued Jun. 11, 2024.

* cited by examiner

*Primary Examiner* — Adam C Milligan
*Assistant Examiner* — Karen Cheng
(74) *Attorney, Agent, or Firm* — Birch, Stewart, Kolasch & Birch, LLP

(57) ABSTRACT

The present application relates to a cis-para-substituted cyclohexylaminonitrile salt represented by formula (I), a preparation method therefor and use thereof as an intermediate for preparing a pesticide, and a method for preparing the pesticide by using same as an intermediate. In the formula, R is $C_{1-10}$ alkyl or $C_{1-10}$alkyloxy, $C_{2-10}$ alkenyl or $C_{2-10}$ alkenyloxy, $C_{2-10}$ alkynyl or $C_{2-10}$ alkynyloxy, $C_{3-10}$ cycloalkyl or $C_{3-10}$ cycloalkyloxy, $C_{3-10}$ heterocycloalkyl or $C_{3-10}$ heterocycloalkyloxy containing 1-2 heteroatoms selected from O and N.

(I)

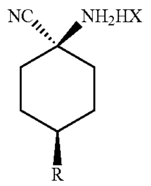

11 Claims, No Drawings

*CIS-PARA*-SUBSTITUTED CYCLOHEXYLAMINONITRILE SALT, PREPARATION METHOD THEREFOR AND USE THEREOF, AND METHOD FOR PREPARING PESTICIDE USING SAME

TECHNICAL FIELD

The present invention relates to a cis-para-substituted cyclohexylaminonitrile salt, a preparation method therefor, the use thereof as an intermediate for preparing a pesticide, and a method for preparing a pesticide by using the same as an intermediate.

BACKGROUND TECHNIQUE

Chinese patent CN103270020B discloses the cis-amino-4-alkoxy cyclohexane carbonitrile salt represented by the following formula,

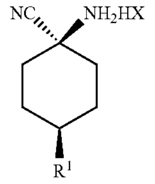

wherein HX is hydrochloric acid, sulfuric acid, phosphoric acid, formic acid, acetic acid, p-toluenesulfonic acid or methanesulfonic acid, and $R^1$ is alkoxy.

However, the inventors of the present application found that the three inorganic acids of hydrochloric acid, sulfuric acid and phosphoric acid used in CN103270020B are not selective, and the cis-isomer compound cannot be selectively crystallized and separated by the salt formation of these acids with amino-4-alkoxycyclohexanecarbonitrile; the salt formed by acetic acid and the above cyclohexanecarbonitrile compound cannot be crystallized; the selectivity of p-toluenesulfonic acid and methanesulfonic acid is poor, which is not conducive to industrial production; the salt formed by formic acid and the above cyclohexanecarbonitrile compound is easy to agglomerate, has poor stability, and is easy to decompose, furthermore, the color of the salt becomes darker and the melting point thereof decreases during storage, which seriously affects the subsequent use of the product.

In Chinese patent CN110691771A, the above HX is changed into maleic acid and glycolic acid, and obtained good selectivity and product stability.

SUMMARY OF THE INVENTION

The inventors of the present application have found in practice that maleic acid and glycolic acid are difficult to be recycled and reused because they are easily soluble in water. Therefore, the inventors of the present application conducted further research on the selection and optimization of the above HX acid, and based on which the present invention was obtained.

One aspect of the present application relates to a cis-para-substituted cyclohexylaminonitrile salt represented by the following formula (I):

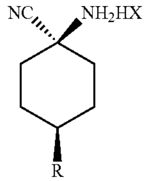

(I)

In the above formula (I), the para-substituent R is $C_{1-10}$ alkyl or $C_{1-10}$ alkyloxy, $C_{2-10}$ alkenyl or $C_{2-10}$ alkenyloxy, $C_{2-10}$ alkynyl or $C_{2-10}$ alkynyloxy, $C_{3-10}$ cycloalkyl or $C_{3-10}$ cycloalkyloxy, $C_{3-10}$ heterocycloalkyl or $C_{3-10}$ heterocycloalkyloxy containing 1-2 heteroatoms selected from O and N;

HX is benzoic acid, p-nitrobenzoic acid, m-nitrobenzoic acid, p-toluic acid or salicylic acid.

Another aspect of the present application relates to a method of preparation for the cis-para-substituted cyclohexylaminonitrile salt of formula (I) above, which comprises adding benzoic acid, p-nitrobenzoic acid, m-nitrobenzoic acid, p-toluic acid or salicylic acid into a solution of the cis/trans para-substituted cyclohexylaminonitrile compound in an organic solvent, stirring and crystallizing, and then separating to obtain the compound of formula (I) in a solid form.

The present application also relates to the use of the cis-para-substituted cyclohexylaminonitrile salt of formula (I) as an intermediate for preparing a pesticide, such as spirotetramat.

The present application further relates to a method for preparing compound (II), in which the cis-para-substituted cyclohexylaminonitrile salt of formula (I) is used as a raw material, and the compound (II) is prepared by the following reaction:

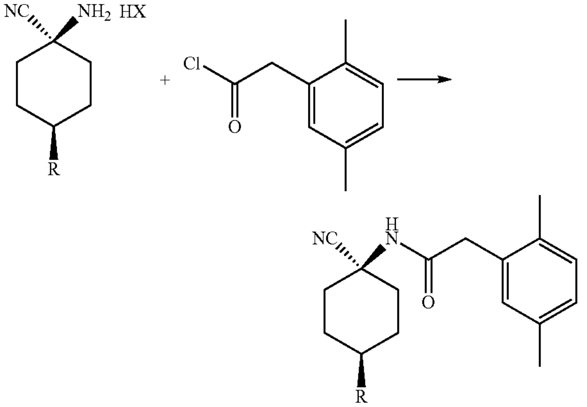

(II)

DETAILED DESCRIPTION OF THE INVENTION

In this application, unless otherwise specified, "%" means weight percentage.

In the above formula (I), R is $C_{1-10}$ alkyl or $C_{1-10}$ alkyloxy, $C_{2-10}$ alkenyl or $C_{2-10}$ alkenyloxy, $C_{2-10}$ alkynyl or $C_{2-10}$ alkynyloxy, $C_{3-10}$ cycloalkyl or $C_{3-10}$ cycloalkyloxy, $C_{3-10}$ heterocycloalkyl or $C_{3-10}$ heterocycloalkyloxy containing 1-2 heteroatoms selected from O and N, preferably $C_{1-6}$ alkyl or $C_{1-6}$ alkyloxy, $C_{2-6}$ alkenyl or $C_{2-6}$ alkenyloxy, $C_{2-6}$ alkynyl or $C_{2-6}$ alkynyloxy, $C_{3-6}$ cycloalkyl or $C_{3-6}$ cycloalkyloxy, $C_{3-6}$ heterocycloalkyl or $C_{3-6}$ heterocycloalkyloxy containing 1-2 heteroatoms selected from O and N, furthermore more preferably $C_{1-6}$ alkyl or $C_{1-6}$ alkyloxy, particularly preferably methyl or methoxy.

HX is benzoic acid, p-nitrobenzoic acid, m-nitrobenzoic acid, p-toluic acid or salicylic acid, preferably benzoic acid or salicylic acid, particularly preferably benzoic acid.

Compared with maleic acid and glycolic acid, using the above acids as HX makes the salt forming by crystallization faster, and the crystallized product is loose and not easy to harden, with fast filtration and easy to rinse.

In addition, when the compound of formula (I) is used as an intermediate for subsequent reactions, HX will dissociate and return to a free acid, which needs to be recycled and reused as much as possible for environmental and raw material cost reasons. Maleic acid and glycolic acid are difficult to be recycled because of their good water solubility. Another advantage of using benzoic acid, p-nitrobenzoic acid, m-nitrobenzoic acid, p-toluic acid and salicylic acid as HX is that these acids are slightly soluble or insoluble in water and precipitate in the aqueous phase after dissociation, and thus is easily recycled and reused.

Further, such as in the above reaction for preparation of formula (II) compound, an acid binding agent is required to neutralize the free HX. Another advantage of using benzoic, p-nitrobenzoic, m-nitrobenzoic, p-toluic and salicylic acids as HX is that these acids are monoacids, which allows to reduce the amount of acid binding agent compared to the dibasic maleic acid.

By reacting cis/trans mixture of the para-substituted cyclohexylaminonitrile compound with benzoic acid, p-nitrobenzoic acid, m-nitrobenzoic acid, p-toluic acid or salicylic acid to form salts, these acids preferentially react with the cis-isomer, and the obtained cis-isomer salts are insoluble in the solvent and precipitate as a solid, thereby selectively separating the cis-isomer as a solid salt.

The cis-isomer is the predominant isomer. Therefore, the higher the cis-isomer ratio and the lower the trans-isomer ratio in the solid precipitate, the better. Preferably, the ratio of cis/trans in the solid precipitate is more than 90:10, more preferably 95:5 or more, and further preferably 96:4 or more.

On the other hand, the lower the cis:trans ratio in the filtrate, the better. Preferably, the ratio of cis:trans in the filtrate is less than 30:70.

A method of preparation for compound (I) of the present invention comprises the following steps: dissolving the cis/trans para-substituted cyclohexylaminonitrile compound in an organic solvent, and then adding benzoic acid, p-nitrobenzoic acid, m-nitrobenzoic acid, p-toluic acid or salicylic acid, stirring and crystallizing, separating the precipitated solid to obtain the compound of formula (I).

The cis/trans para-substituted cyclohexylaminonitrile as the raw material compound used in the above preparation method of the present invention can be synthesized by, for example, the well-known Strecker reaction, or can also be synthesized by a known method disclosed in, for example, Chinese Patent Document CN103270020B.

The organic solvent includes but not limited to toluenes, ethers, alkanes or halogenated hydrocarbons, specific examples include but not limited to toluene, xylene, chlorobenzene, methyl tert-butyl ether, cyclohexane, methylcyclohexane, tetrahydrofuran, dichloromethane, tetrachloroethylene and the like. The solvent may be used alone or in combination of two or more.

The amount of the organic solvent used is preferably 1-10 times by mass, more preferably 2-5 times by mass, and further more preferably 3-4 times by mass, relative to the cis/trans para-substituted cyclohexylaminonitrile compound.

When the amount of benzoic acid, p-nitrobenzoic acid, m-nitrobenzoic acid, p-toluic acid or salicylic acid added is too small, the cis-isomer in cis/trans raw material mixture cannot be fully reacted and separated, and when too much is added, more trans-isomer will be involved in the reaction. Therefore, the added amount of the above acid is preferably 0.8~1.5 mole times, more preferably 1.0~1.3 mole times the total amount of cis-isomer in the cis/trans raw material mixture.

In the above preparation method of the present invention, stirring and crystallizing temperature is preferably 0~40° C., more preferably 10~30° C., particularly preferably 15~20° C. The stirring and crystallizing time is preferably 2~6 hours.

Preferably, ultrasonication is performed while stirring and crystallizing to accelerate crystallization and improve separation selectivity, especially when salicylic acid is used as the crystallizing acid.

The precipitated solid can be separated by filtration or other means. When benzoic acid, p-nitrobenzoic acid, m-nitrobenzoic acid, p-toluic acid or salicylic acid is used, the obtained crystalline salt is loose, hard to harden and easy to filter.

The compound of formula (I) in the present invention is an important intermediate compound that can be used for the preparation of, for example, spirotetramat.

The compound of formula (I) in the present invention can react with acyl halide in the presence of acid binding agent, for example, reacts with 2,5-dimethylphenylacetyl chloride as follows to obtain compound (II):

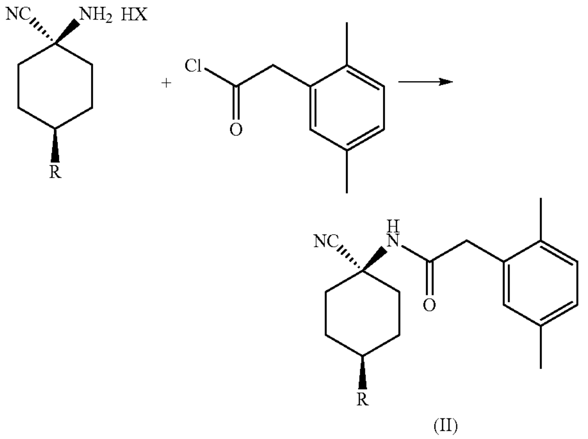

(II)

In the above formula, HX and R are the same as defined above.

A salt of an alkali metal or alkaline earth metal or an organic amine and the like can be used as the acid binding agent. As specific examples, sodium hydroxide, sodium carbonate, sodium bicarbonate, triethylamine and the like can be listed.

The above reaction is preferably carried out in water and any organic solvent immiscible with water. The organic solvent is preferably one selected from toluene, xylene, dichloromethane, dichloroethane, tetrachloroethylene, ethyl acetate, isopropyl acetate, or a mixture thereof; The ratio of water to the organic solvent is preferably 1-5:5-1. The above reaction is preferably carried out at 0-30° C., more preferably at 0-15° C.

EXAMPLES

Example 1 Resolution of a Mixture of Cis/Trans Isomers of 4-methoxy-1-cyanocyclohexylamine Took 300 g of xylene solution of a mixture of cis/trans isomers of 4-methoxy-1-cyanocyclohexylamine (cis: trans=55:45) containing 48 g of cis-isomer respectively, relative to the amount of cis-isomer in the mixture, added 1 mole equivalent of acid listed in Table 1 respectively, stirred and crystallized at room temperature, and the precipitated solid was filtered and rinsed with xylene. 2,5-dimethylphenylacetyl chloride and triethylamine were added to the filtrate, and the solid was dissolved in dichloromethane followed by an addition of 2,5-dimethylphenylacetyl chloride and triethylamine. Thus, the cyanamide compound in the filtrate and solid was amidated to produce the compound shown in formula (II), then detected by HPLC to determine cis/trans ratio. The results are shown in Table 1.

A higher cis/trans ratio in the obtained crystalline solid and a lower cis/trans ratio in the filtrate implies a better selectivity of crystallization separation.

HPLC Detection Conditions

Mobile phase: methanol:water (adjusted to pH 2.5-2.7 by formic acid)=70:30

Chromatographic column: C18

Column temperature: 30° C.

Wavelength: 210 nm

Flow rate: 1.0 ml/min

TABLE 1

| Acid | Crystallization time | Cis/trans ratio in solid | Cis/trans ratio in filtrate | Crystallization effect |
|---|---|---|---|---|
| maleic acid | 7 h | 94.81/5.19 | 33.73/66.27 | The obtained crystalline solid was filtered slowly and was not easily rinsed. |
| salicylic acid | 3 h | 93.28/6.72 | 47.01/52.99 | The crystallization speed was faster than that of maleic acid, the obtained crystalline solid was loose and filtered quickly and rinsed easily, but the cis/trans ratio in the solid was relatively low, while that in the filtrate was relatively high. |
| benzoic acid | 3 h | 96.27/3.73 | 27.15/72.85 | The crystallization speed was faster than that of maleic acid, the obtained crystalline solid was loose, the filtration rate was faster than that of salicylic acid, and it was easy to rinse. Crystals are observed to be rod-shaped under a microscope, and the cis/trans ratio in both the solid and the filtrate reached a desired range. |
| m-nitrobenzoic acid | 2 h<br>6 h | 93.25/6.75<br>95.18/4.82 | 24.03/75.97<br>23.38/76.62 | The crystallization time was slightly longer than that of benzoic acid, and the properties of the obtained crystalline solid were similar to those of benzoate, easy to filter, fast to filter, and the cis/trans ratio in both solid and filtrate reached a desired range. |
| p-nitrobenzoic acid | 1.5 h<br>3.5 h | 94.03/5.97<br>96.12/3.88 | 21.05/78.95<br>20.73/79.27 | The crystallization time was equivalent to that of benzoic acid, the properties of the obtained crystalline solid were similar to those of benzoate, easy to filter, fast to filter, and the cis/trans ratio in both solid and filtrate reached a desired range. |
| m-toluic acid | 3 h<br>6 h | 95.32/4.68<br>95.96/4.04 | 32.76/67.34<br>33.59/66.41 | The crystallization time was slightly longer than that of benzoic acid, and the cis/trans ratio in the filtrate was slightly higher. The properties of the obtained crystalline solid were similar to those of benzoate, easy to filter and fast to filter. |
| p-toluic acid | 2 h<br>4 h<br>6 h | 91.03/8.97<br>94.96/5.04<br>96.51/3.49 | 33.92/66.08<br>20.97/79.03<br>19.79/80.21 | The crystallization time was slightly longer than that of benzoic acid, and the |

TABLE 1-continued

| Acid | Crystallization time | Cis/trans ratio in solid | Cis/trans ratio in filtrate | Crystallization effect |
|---|---|---|---|---|
| | | | | properties of the obtained crystalline solid was similar to those of benzoate, easy to filter, fast to filter, and the cis/trans ratio in both solid and filtrate reached a desired range. |
| p-ethylbenzoic acid | 1.5 h | 92.27/7.73 | 31.65/68.35 | The cis/trans ratio in the solid was slightly lower, the cis/trans ratio in the filtrate was slightly higher, and the separation selectivity was slightly poor. |
| | 3 h | 91.77/8.23 | 31.38/68.62 | |
| | 4.5 h | 94.01/5.99 | 30.92/69.08 | |

Example 2 Resolution of a Mixture of Cis/Trans Isomers of 4-methoxy-1-cyanocyclohexylamine Took 750 g of xylene solution of a mixture of cis/trans isomers of 4-methoxy-1-cyanocyclohexylamine (cis: trans=55:45) containing 105 g of cis-isomer, respectively, relative to the amount of cis-isomer in the mixture, added 1 mole equivalent of acid listed in Table 2 respectively, stirred and crystallized at 15~20° C. Samples were taken separately at different time points, filtered, and the filtered solid was rinsed with xylene. Cis/trans ratio of solid and filtrate was detected by HPLC in the same way as in Example 1. The results are shown in Table 2.

TABLE 2

| time of | maleic acid | | salicylic acid | |
|---|---|---|---|---|
| crystallization with ultrasonic stirring | cis/trans ratio in solid | cis/trans ratio in filtrate | cis/trans ratio in solid | cis/trans ratio in filtrate |
| 1 h | 84.35/15.65 | 40.09/59.91 | 95.37/4.63 | 25.08/74.92 |
| 2.5 h | 86.81/13.19 | 34.91/65.09 | 96.51/3.49 | 24.39/75.61 |
| 5.5 h | 95.37/4.63 | 17.86/82.14 | 97.14/2.86 | 28.34/71.66 |

It can be seen from Table 2 that the crystallization speed can be accelerated by ultrasonic-assisted crystallization, and it helps to improve the separation selectivity.

INDUSTRIAL APPLICABILITY

The method of the present invention can separate cis/trans-p-methoxy cyclohexylaminonitrile with good selectivity to obtain cis-para-substituted cyclohexylaminonitrile salt, which is an important intermediate for the synthesis of a pesticide such as spirotetramat.

The invention claimed is:

1. A cis-para-substituted cyclohexylaminonitrile salt represented by the following formula (I):

(I)

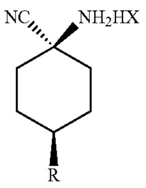

wherein the para-substituent R is $C_{1-6}$ alkyl or $C_{1-6}$ alkyloxy, and

HX is benzoic acid, p-nitrobenzoic acid, or salicylic acid.

2. A method of preparation for the cis-para-substituted cyclohexylaminonitrile salt of formula (I) as claimed in claim 1, which comprises adding benzoic acid, p-nitrobenzoic acid, or salicylic acid into a solution of the cis/trans para-substituted cyclohexylaminonitrile compound in an organic solvent, stirring and crystallizing, and then separating to obtain the compound of formula (I) in a solid form.

3. The method of preparation as claimed in claim 2, wherein relative to the cis/trans para-substituted cyclohexylaminonitrile compound, the amount of organic solvent is 2-5 mass times.

4. The method of preparation as claimed in claim 2, wherein the organic solvent is one or two or more selected from toluene, xylene, chlorobenzene, methyl tert-butyl ether, cyclohexane, methylcyclohexane, tetrahydrofuran, dichloromethane, and tetrachloroethylene.

5. The method of preparation as claimed in claim 2, wherein relative to the amount of cis-isomer in the cis/trans para-substituted cyclohexylaminonitrile compound, the added amount of benzoic acid, p-nitrobenzoic acid, or salicylic acid is 0.8~1.5 mole times.

6. The method of preparation as claimed in claim 2, wherein the time for stirring and crystallizing is 2-6 hours.

7. The method of preparation as claimed in claim 2, wherein ultrasonication is performed while stirring and crystallizing.

8. The cis-para-substituted cyclohexylaminonitrile salt of formula (I) as claimed in claim 1, wherein the para-substituent R is methyl or methoxy.

9. The method of preparation as claimed in claim 5, wherein relative to the amount of cis-isomer in the cis/trans para-substituted cyclohexylaminonitrile compound, the added amount of benzoic acid, p-nitrobenzoic acid, or salicylic acid is 1.0~1.3 mole times.

10. A method of preparing a compound of formula (II), wherein said method comprises reacting the cis-para-substituted cyclohexylaminonitrile salt of claim 1 with 2,5-dimethylphenylacetyl chloride in the presence of a diluent and an acid binding agent, thereby obtaining compound (II):

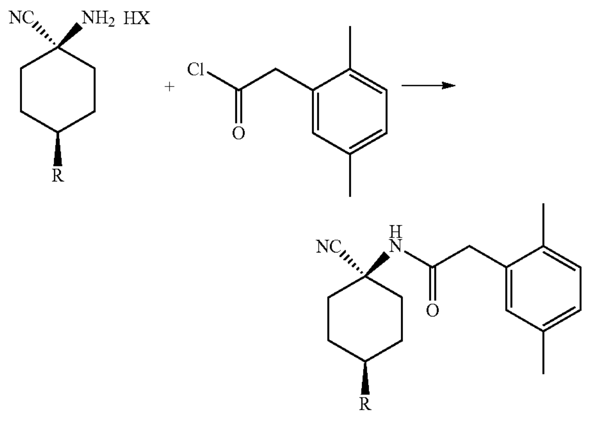
(II)
wherein HX and R are as defined in claim 1.
11. The method of claim 10, wherein the compound of formula (II) is spirotetramat.
* * * * *